United States Patent
Persson (10) Patent No.: US 8,991,394 B2
(45) Date of Patent: Mar. 31, 2015

(54) BREATHING PROTECTOR

(75) Inventor: Jan-Ove Persson, Höör (SE)

(73) Assignee: Atos Medical AB (SE)

( * ) Notice: Subject to any disclaimer, the term of this patent is extended or adjusted under 35 U.S.C. 154(b) by 797 days.

(21) Appl. No.: 13/130,246

(22) PCT Filed: Nov. 27, 2009

(86) PCT No.: PCT/EP2009/065961
§ 371 (c)(1),
(2), (4) Date: May 19, 2011

(87) PCT Pub. No.: WO2010/060983
PCT Pub. Date: Jun. 3, 2010

(65) Prior Publication Data
US 2011/0220108 A1    Sep. 15, 2011

(30) Foreign Application Priority Data

Nov. 28, 2008 (SE) .................................. 0850108-2

(51) Int. Cl.
| A61M 11/00 | (2006.01) |
| A62B 9/02 | (2006.01) |
| A61F 2/20 | (2006.01) |
| A61M 16/10 | (2006.01) |
| A61M 16/04 | (2006.01) |

(52) U.S. Cl.
CPC ....... A61M 16/1045 (2013.01); A61M 16/0468 (2013.01); A61F 2/20 (2013.01)
USPC ............ 128/205.24; 128/205.27; 128/207.16; 128/201.13; 623/9

(58) Field of Classification Search
CPC ............ A61M 16/00; A61M 16/0465; A61M 16/0468; A61M 16/0472; A61M 16/20; A61M 16/206; A61M 16/201; A61M 16/208; A61M 2205/75; A61M 2210/1028; A61M 2210/1032; F16K 21/04

USPC ............ 128/200.24, 200.26, 201.13, 201.28, 128/205.24, 205.27, 207.14–207.16; 137/903; 210/429, 431, 432; 251/320, 251/321; 623/9

See application file for complete search history.

(56) References Cited

U.S. PATENT DOCUMENTS

| 731,973 A | * | 6/1903 | Teter .......................... 128/207.13 |
| 5,022,394 A | * | 6/1991 | Chmielinski ............. 128/207.14 |
| 5,203,372 A | * | 4/1993 | Freiler ........................... 137/469 |
| 5,738,095 A | * | 4/1998 | Persson ..................... 128/207.14 |

(Continued)

FOREIGN PATENT DOCUMENTS

| WO | WO-99/29268 A1 | 6/1999 |
| WO | WO-99/60954 A1 | 12/1999 |
| WO | WO-2008/132222 A2 | 11/2008 |

*Primary Examiner* — Justine Yu
*Assistant Examiner* — Douglas Sul
(74) *Attorney, Agent, or Firm* — Rader, Fishman & Grauer PLLC (57) ABSTRACT

A breathing protector may include a filter housing having a central axis, a distal end, a proximal end, a first opening and a second opening. The second opening may be located in a proximal end of the filter housing and the first opening may be located distally of the second opening, such that the first opening is located upstream of the second opening. An exchanging filter may be disposed in the filter housing and a valve seat may extend around the first opening. A rail, located circumferentially of the valve seat, may extend axially and distally away from the first opening. The rail may include a distal end and at least one rib. A valve member may be arranged in a transversal plane to the central axis and engage the valve seat in a closed position. A return spring may press the valve member into the open position.

19 Claims, 4 Drawing Sheets

(56) References Cited

U.S. PATENT DOCUMENTS

| | | | |
|---|---|---|---|
| 6,422,235 B1 * | 7/2002 | Persson | 128/200.26 |
| 6,772,758 B2 | 8/2004 | Lambert | |
| 8,443,806 B2 * | 5/2013 | Morelli et al. | 128/207.12 |
| 2013/0192602 A1 * | 8/2013 | Leibitzki et al. | 128/205.27 |

* cited by examiner

BREATHING PROTECTOR

CROSS-REFERENCES TO RELATED APPLICATION

This application claims priority to European Patent Application 0850108-2 filed on Nov. 28, 2008 and PCT/EP2009/065961 filed on Nov. 27, 2009, which are hereby incorporated by reference in their entireties.

TECHNICAL FIELD

This invention pertains in general to the field of a breathing protector for use in a stoma of a laryngectomized or tracheotomised person, said breathing protector having a housing with at least one inlet and at least one outlet, such that an air flow in use will pass from the surroundings of said person through said inlet to said outlet, into trachea of said person, said breathing protector comprising a heat-moisture exchanger in said housing in between the at least one inlet and the at least one outlet, such that the air flow will pass through said heat-moisture exchanger when said air flow in use passes through said inlet to said outlet.

BACKGROUND

A tracheostomy is a surgical procedure in which an opening is formed through the anterior surface of the neck into the trachea. The opening is referred to as a tracheostoma. A tracheostomy tube can be provided to extend between the tracheostoma and the trachea. A tracheotomy is performed for example when there is a malfunction, such as a result from injury or disorder, in respect of the nervous system or the respiratory passages, which malfunction results in an incapacity to obtain enough air. An inferior lung capacity or need of respiratory treatment may also result in a tracheotomy.

A laryngectomy is a surgical procedure, used for example to treat a carcinoma, which involves removal of the larynx or voice box and the creation of a tracheostoma. A consequence of the procedure is that the trachea is no longer connected to the pharynx but is diverted to the tracheostoma. After this procedure, normal nasal function is not possible. In a subject whose breathing functions normally, the nose and the mucous membrane lining of the nasal cavity perform important functions in conditioning inhaled air. The convoluted passages and rich blood supply serve to increase both the temperature and humidity of the inhaled air to minimise the differential in these parameters with those of the surface of the lungs. Normally some heat and moisture is also captured from exhaled air prior to its release to the atmosphere. The mucous lining of the nasal passages also serves to remove particulate matter, such as fine dust particles, pollutants and microorganisms, from the inhaled air, and the action of cilia transports mucous and any particles away from the lungs.

When a patient has received a laryngectomy, in effect all inhaled air enters the lungs via the tracheostoma, and the nose is effectively not involved in the inhalation process. Exhaled air may pass through the tracheostoma or, if a voice prosthesis has been fitted, the stoma can be occluded so that the exhaled air is diverted through the voice prosthesis into the pharynx and the mouth, enabling the patient to speak. It is desirable that the flow of the exhaled air be controlled by means of a tracheostoma valve. In these situations, the valve can be arranged to remain open during breathing but, with a small additional increase in exhaled air flow, can be closed to divert the airflow.

In this respect filter devices and breathing protectors have been developed to enable moisturizing of inhaled air and removal of small particles and bacteriological substances in said inhaled air. This is to resemble the functions of a nose. However, there are several complications related to the manufacturing of such devices. Firstly, the user of such devices is in need of good moisturizing and filtering effect while keeping the size, such as the surface area, of the device as small as possible. Secondly, the moisturizing effect and filtering effect is in need of large surface area, while not creating a too large resistance over the device. These criterions are contradictive, which the observant reader already has acknowledged. Also, a person with a laryngectomy has to hold his finger over these devices when wishing to speak, to thereby obstruct the air flow through the device and the stoma through the tracheal wall, which will burden the filter with undue contamination, due to transfer of impurities from the finger of the user to the filter. Also, if a patient turns unconscious, clothing etc may hinder air-flow through the device.

U.S. Pat. No. 5,738,095 discloses a device with a push button, in form of a disc, displaceable along a central axis of the device by the aid of a centrally located piston, such disc being operable against a spring mechanism to cooperate with a valve seat in the proximal end of the device. The device according to U.S. Pat. No. 5,738,095 is also provided with an axially extending rail in the distal end of the device, to only allow closing force in the axial direction and acting from above within the cross-sectional area of the device, thus providing a safe mechanism for minimizing risk for occlusion of the device. However, the centrally located piston and the spring mechanism decrease the effective volume of the filter within the device. Also, the technical field would benefit of a spring mechanism that is easier to manufacture.

U.S. Pat. No. 6,772,758 discloses a breathing protector to be applied over a tracheostoma, including a heat-moisture exchanger body which communicates with the tracheostoma through an inlet. A closing lid is attached to the heat-moisture exchanger, and can be pressed down to close the communication by cooperating directly with a valve seat or by squeezing the heat-moisture exchanger against the valve seat. However, there is a need for glue in between the heat-moisture exchanger and the lid. Furthermore, a part of the heat-moisture exchanger has to be excluded for the lid to cooperate directly with the valve seat, otherwise the heat-moisture exchanger has to be squeezed in between the lid and the valve seat, which strains the heat-moisture exchanger unnecessarily and impairs the closing action. Also, the device according to U.S. Pat. No. 6,772,758 lacks an axially extending rail in the distal end of the device, to only allow closing force in the axial direction and acting from above within the cross-sectional area of the device.

Hence, an improved breathing protector would be advantageous and in particular a breathing protector allowing for maximized moisturizing effect in the space provided in the housing of the breathing protector, while also providing the possibility to a patient to keep the breathing protector closed, such as during speech, without undue contamination of the filter by holding a finger over said opening during the entire period of speech, and without undue substances, such as glue, prone to degradation in moist environment and repeated strain. It would also be advantageous to provide a breathing protector allowing for an excellent moisturizing effect, while still providing a small breathing protector with a satisfactory resistance over said breathing protector, and with a spring mechanism that is easier to manufacture, while simultaneously minimizing the risk for occlusion of the breathing protector.

SUMMARY

Accordingly, the present invention seeks to mitigate, alleviate or eliminate one or more of the above-identified deficiencies and to provide an improved breathing protector of the kind referred to. For this purpose the breathing protector is characterized in that the resiliency of the heat-moisture exchanging filter forces the lid into the open position.

Advantageous features of the invention are defined in the dependent claims.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DETAILED DESCRIPTION

The following description focuses on embodiments of the present invention applicable to a breathing protector and in particular to a breathing protector for use in a stoma of a laryngectomized or tracheotomised person, where said stoma is communicating with trachea of said person.

Figure 1:
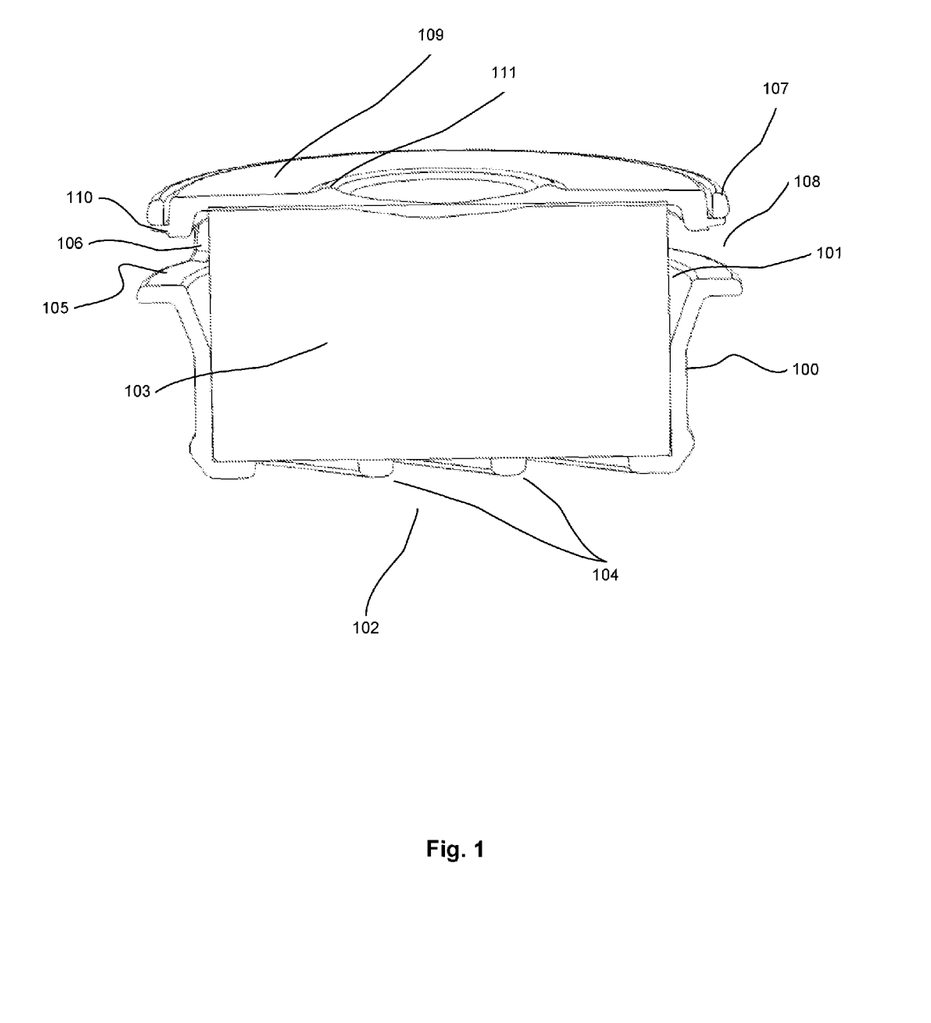
FIG. 1 is a cross sectional view of a breathing protector according to an embodiment of the present invention.
Figure 2A:
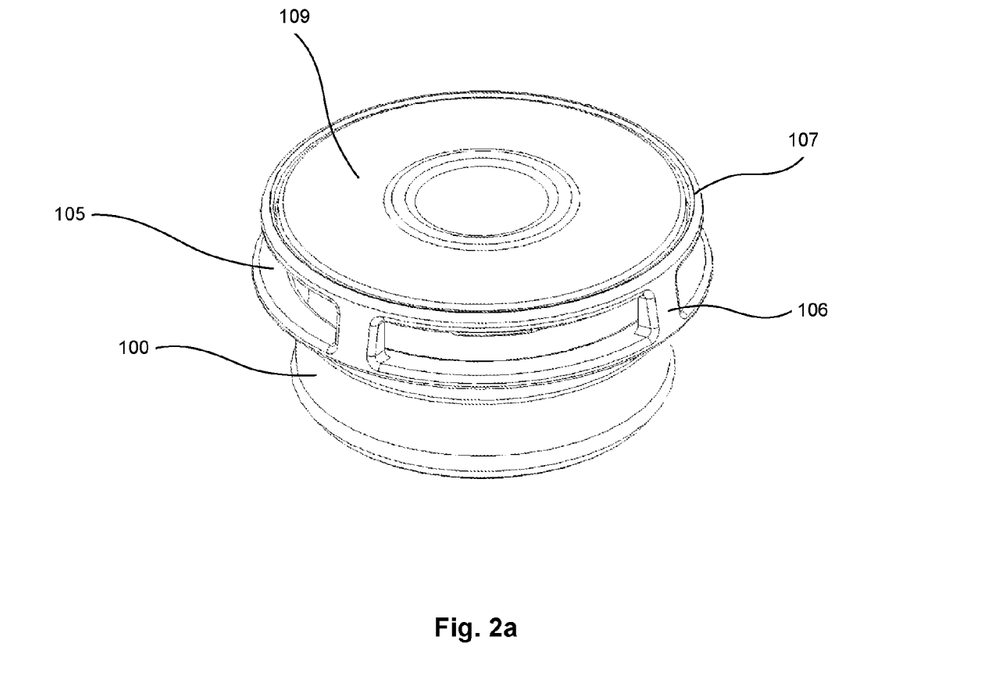
FIGS. 2a and 2b are elevated views of the breathing protector according to the embodiment of FIG. 1.
Figure 2B:
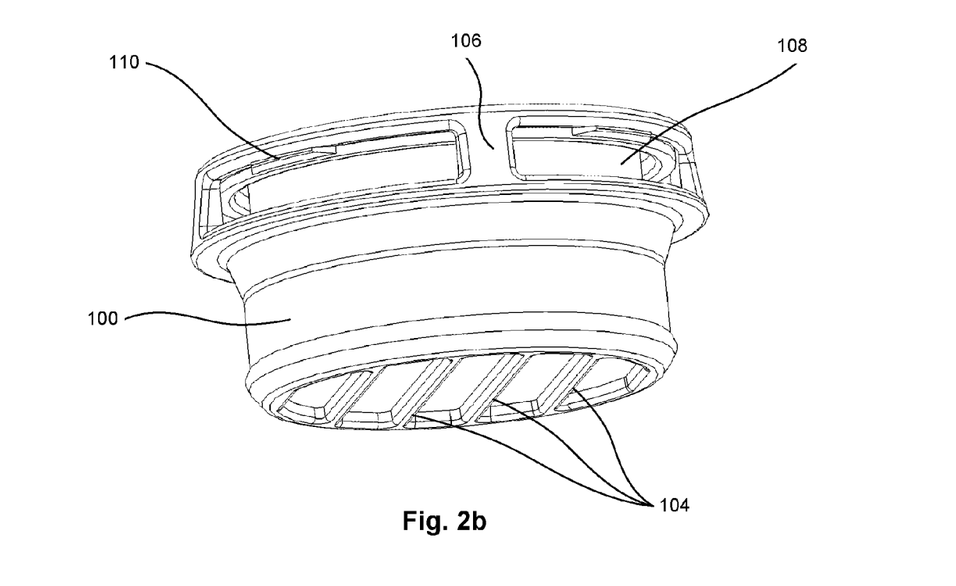

The device according to one embodiment of the invention is shown in FIGS. 1, 2a and 2b, said device comprising a cylindrical filter housing 100. The device may be a breathing protector for use in a stoma of a laryngectomized or tracheotomised person.

The cylindrical filter housing 100 has a distal and a proximal end, and a central axis from one end to the other. The cylindrical filter housing 100 has a first opening 101 and a second opening 102, such that an air flow in use will pass from the surroundings of a patient through said first opening 101 to said second opening 102, into trachea of said patient. The second opening 102 is located in the proximal end of the device. The second opening 102 may thus be located in a proximal end of said filter housing 100, and said first opening 101 is located distally of said second opening 102, such that said first opening 101 is located upstream said second opening 102 during inhalation. A heat-moisture exchanging filter 103 is received in said cylindrical filter housing 100. The second opening 102 of the filter housing 100 may be provided with radial or diagonal arms 104, forming a stop element for the heat-moisture exchanging filter 103. The openings between the radial or diagonal arms 104 and the periphery of the second opening 102 constitute outlets of breathing air during inhalation, and consequently inlets of breathing air during exhalation. When the second opening 102 of the filter housing 100 is provided with arms 104, extending across the second opening 102, these arms 104 may hinder proximal movement of the heat-moisture exchanging filter 103. These arms 104 may be arranged in a non-intersecting manner, such as in parallel or substantially parallel, in accordance with FIG. 1b. Arms 104 arranged in this manner simplify cleaning of the second opening 102.

Distally of the second opening 102 of the cylindrical filter housing 100 the first opening 101 is provided. The heat-moisture exchanging filter 103 will then be partly located within said first and second opening when the device is in an open position, and fully located within said first and second opening, when the device is in a closed position. The first opening is encircled by a valve seat 105. Thus, the valve seat 105 is arranged around the first opening. Radially and/or circumferentially outwards from the valve seat 105, a rail is extending axially and distally from said first opening 101. The rail comprises ribs 106, extending axially and distally from the first opening 101. A ring 107 connects the ribs 106 in the distal end of the device. Between the ribs 106, proximally of the ring 107 apertures 108 are provided. The apertures 108 may be perpendicular to the central axis of the housing 100, which may be seen at least in FIG. 1. Apertures 108 constitute outlets of breathing air during exhalation, and consequently inlets of breathing air during inhalation. Thus, the heat-moisture exchanging filter 103 is located in said housing 100 in between the apertures 108 and the second opening 102, such that the air flow will pass through said heat-moisture exchanger 103, when said air flow during inhalation passes through said apertures 108 to said second opening 102.

Proximally of the ring 107 and distally of the valve seat 105 a valve member, such as circular lid 109, is provided. The circular lid 109 has a surface area covering the first opening 101, such that the circular lid 109 peripherally will sit on valve seat 105 to close the first opening 101. The valve member, such as the lid 109, may then be arranged in a transversal plane to the central axis of the device. The valve member is adapted to cloyingly engage with the valve seat 105 in a closed position, said valve member 109 being reciprocatingly arranged within the rail between the closed position and an open position. The circular lid 109 has a diameter allowing for axial displacement, while said circular lid 109 being arranged in a transversal plane in respect of a central axis of the cylindrical filter housing 100, within the ribs 106. The opening of the ring 107 does not allow the lid 109 to pass there through. This may be accomplished if the ring 107 is circular with a diameter smaller than the diameter of the circular lid 109. The circular lid 109 may also be peripherally provided with radially extending protrusions 110, said protrusions 110 engaging with the apertures 108, to stop the axial movement in a distal direction of lid 109. The lid/valve member 109 is thus hindered from distal movement by the rail in the open position.

In one embodiment the rail, such as the ring 107, is provided with inwardly and radially extending protrusions, which may hold the lid 109 in place. In this embodiment there is no need for protrusions 110 on the lid 109, even such a possibility not is excluded, and is well inside the scope of the present invention.

The heat-moisture exchanging filter 103 is of a flexible/resilient material, such as a resilient foam. Furthermore, the size of heat-moisture exchanging filter 103 is adapted to press the lid 109 distally towards and against the ring 107. Thus, the heat-moisture exchanging filter 103 acts both as heat-moisture exchanger and return spring, pressing the lid 109 axially and distally into the open position. In order to generate talk the lid 109 is exposed to a pressure from a finger until the lid 109 sits or rests on the valve seat 105 and covers said first opening 101, whereby the first opening is closed, thus closing the communication between the trachea and the surroundings. The device can be closed in this manner even if it is covered by garments. At the same time the device is prevented from coming loose from the stoma because it is pressed against the throat by the finger during talking.

The radial or diagonal arms 104 and the lid 109, due to the shape thereof, holds heat-moisture exchanging filter 103 in position, while the heat-moisture exchanging filter 103 simultaneously acts as a return spring so that the lid 109 after the pressure having been relieved will resiliently return to an open position thereof.

The ribs 106 and ring 107 reduces the risk of the valve member being inadvertently closed, since a force in an axial and proximal direction within the ring 107 has to be applied to close the valve member. Since the lid 109, in the starting position thereof, is in close contact with the heat-moisture exchanging filter 103, the volume of the heat-moisture exchanging filter 103 may be maximized in the device, and breathing air can pass through the apertures 108 directly into contact with the heat-moisture exchanging filter 103 when the device is open, i.e. when the lid 109 is in the outer non-actuated position thereof.

FIGS. 2a and 2b discloses the embodiment according to FIG. 1 in an elevated view from above and below, respectively, to more clearly identify the diagonal arms 104, the valve seat 105, the ribs 106, the ring 107, the apertures 108, the lid 109, and the protrusions 110.

Figure 3:
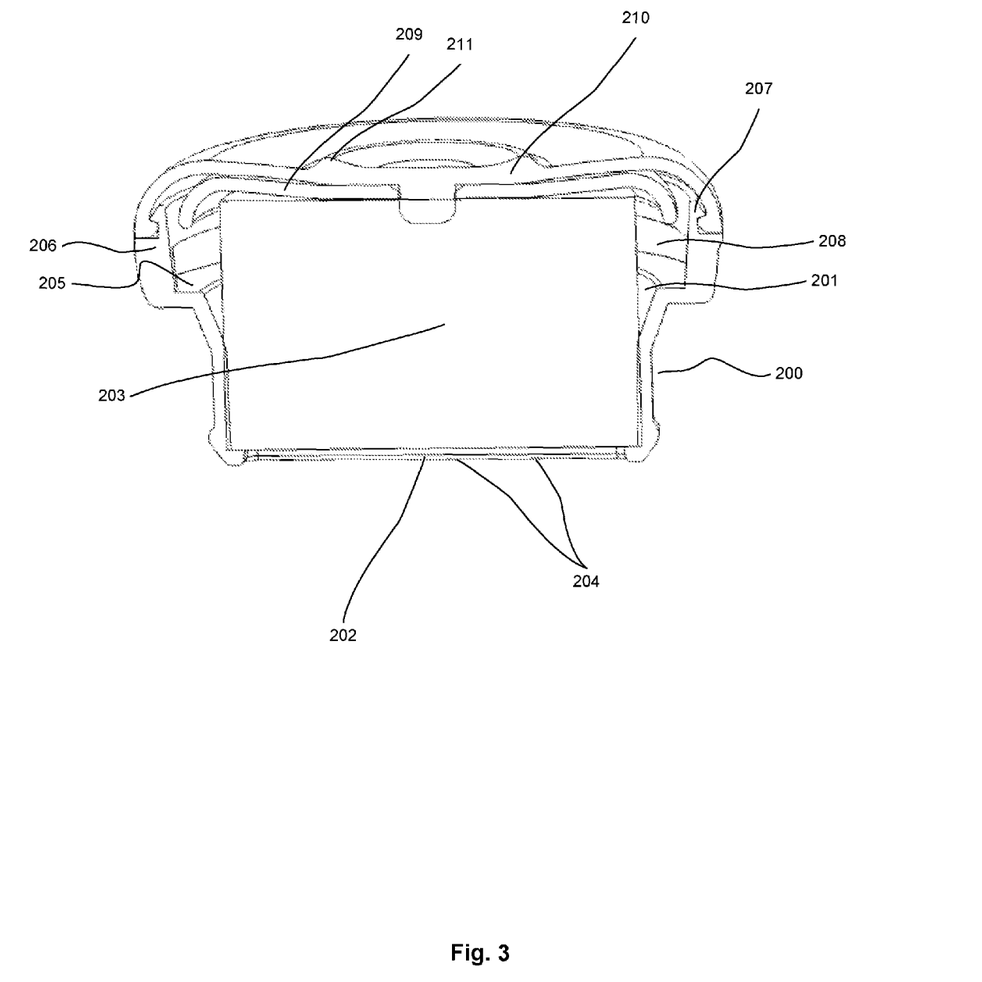
FIG. 3 is a cross sectional view of a breathing protector according to an embodiment of the present invention.

The device according to another embodiment of the invention is shown in FIG. 3, said device comprising a cylindrical filter housing 200. The device may be a breathing protector for use in a stoma of a laryngectomised or tracheotomised person.

The cylindrical filter housing 200 has a distal and a proximal end, and a central axis from one end to the other. The cylindrical filter housing 200 has a first opening 201 and a second opening 202, such that an air flow during inhalation will pass from the surroundings of a patient through said first opening 201 to said second opening 202, into trachea of said patient. The second opening 202 is located in the proximal end of the device. The second opening 202 may thus be located in a proximal end of said filter housing 200, and said first opening 201 is located distally of said second opening 202, such that said first opening 201 is located upstream said second opening 202 during inhalation. A heat-moisture exchanging filter 203 is received in said cylindrical filter housing 200. The second opening 202 of the filter housing 200 may be provided with radial or diagonal arms 204, forming a stop element for the heat-moisture exchanging filter 203. The openings between the radial or diagonal arms 204 and the periphery of the second opening 202 constitute outlets of breathing air during inhalation, and consequently inlets of breathing air during exhalation.

Distally of the second opening 202 of the cylindrical filter housing 200 the first opening 201 is provided. The heat-moisture exchanging filter 203 will then be partly located within said first and second opening when the device is in an open position, and fully located within said first and second opening, when the device is in a closed position. The first opening is encircled by a valve seat 205. Thus, the valve seat 205 is arranged around the first opening. Radially and/or circumferentially outwards from the valve seat 205, a rail is extending axially and distally from said first opening 201. The rail comprises ribs 206, extending axially and distally from the first opening 201. A ring 207 connects the ribs 206 in the distal end of the device. Between the ribs 206, proximally of the ring 207 apertures 208 are provided. Apertures 208 constitute outlets of breathing air during exhalation, and consequently inlets of breathing air during inhalation. The heat-moisture exchanging filter 203 is located in said housing 200 in between the apertures 208 and the second opening 202, such that the air flow will pass through said heat-moisture exchanger 203, when said air flow during inhalation passes through said apertures 208 to said second opening 202.

Substantially in the same transversal plane as the ring 207 and distally of the valve seat 205 a valve member, such as circular lid 209, is provided. The circular lid 209 has a surface area covering the first opening 201, such that the circular lid 209 peripherally will sit or rest on valve seat 205 to close the first opening 201. The circular lid 209 has a diameter allowing for axial displacement, while said circular lid 209 being arranged in a transversal plane in respect of the cylindrical filter housing 200, within the ribs 206. The circular lid 209 is attached to a circular flexible cover 210. The resilience of the flexible cover 210 allows the flexible cover 210 to be pressed down, axially in a proximal direction, to force the lid 209 to closingly fit with the valve seat 205, while still being attached to the ring 207. The valve member, such as the lid 209, may then be arranged in a transversal plane to the central axis of the device. The valve member is adapted to closingly engage with the valve seat 205 in a closed position, said valve member 209 being reciprocatingly arranged within the rail between the closed position and an open position. The lid/valve member 209 is thus hindered from distal movement by the rail in the open position.

According to another embodiment the circular lid 209 is peripherally provided with radially extending protrusions, said protrusions engaging with the apertures 208, to stop the axial movement in a distal direction of lid 209. This may relieve the flexible cover 210 from undue strain, and may keep the lid 209 in place even if the attachment means, such as glue or snap-in function, between the flexible cover 210 and ring 207 breaks. The combination of the lid 209 and the flexible cover 210 provides a distinct interaction between the lid 209 and the valve seat 205, while simultaneously providing the possibility to alter the appearance of the breathing protector, in excess of the advantages presented below. The flexible cover 210 may for example smoothen the outer surface of the breaching protector, minimizing abrasion on fingers. Also, the flexible cover 210 can minimize the risk of foreign objects getting stuck in between the rail and the lid 209, which may impair breathing.

The circular flexible cover 210 is peripherally attached to the ring 207. The heat-moisture exchanging filter 203 is of a flexible/resilient material, such as a resilient foam. Furthermore, the size of heat-moisture exchanging filter 203 is adapted to press the lid 209 distally towards and against the circular flexible cover 210. Thus, the heat-moisture exchanging filter 203 acts both as heat-moisture exchanger and return spring, pressing the lid 209 axially and distally into the open position. In order to generate talk the lid 209 is exposed to a pressure from a finger until the lid 209 sits on the valve seat 205 and covers said first opening 201, whereby the first opening is closed, thus closing the communication between the trachea and the surroundings. The device can be closed in this manner even if it is covered by garments. At the same time the device is prevented from coming loose from the stoma because it is pressed against the throat by the finger during talking.

The radial or diagonal arms 204 and the circular flexible cover 210, due to the shape thereof, holds heat-moisture exchanging filter 203 in position, while the heat-moisture exchanging filter 203 simultaneously acts as a return spring so that the lid 209 after the pressure having been relieved will resiliently return to an open position thereof, in which open position the lid 209 is distally stopped by circular flexible cover 210.

The ribs 206 and ring 207 reduces the risk of the valve member being inadvertently closed, since a force in an axial and proximal direction within the ring 207 has to be applied to close the valve member. Since the lid 209, in the starting and open position thereof, is in close contact with the heat-moisture exchanging filter 203, the volume of the heat-moisture exchanging filter 203 may be maximized in the device, and inhaled breathing air can pass through the apertures 208 directly into contact with the heat-moisture exchanging filter 203 when the device is open, i.e. when the lid 209 is in the outer non-actuated and open position thereof.

Figure 4:
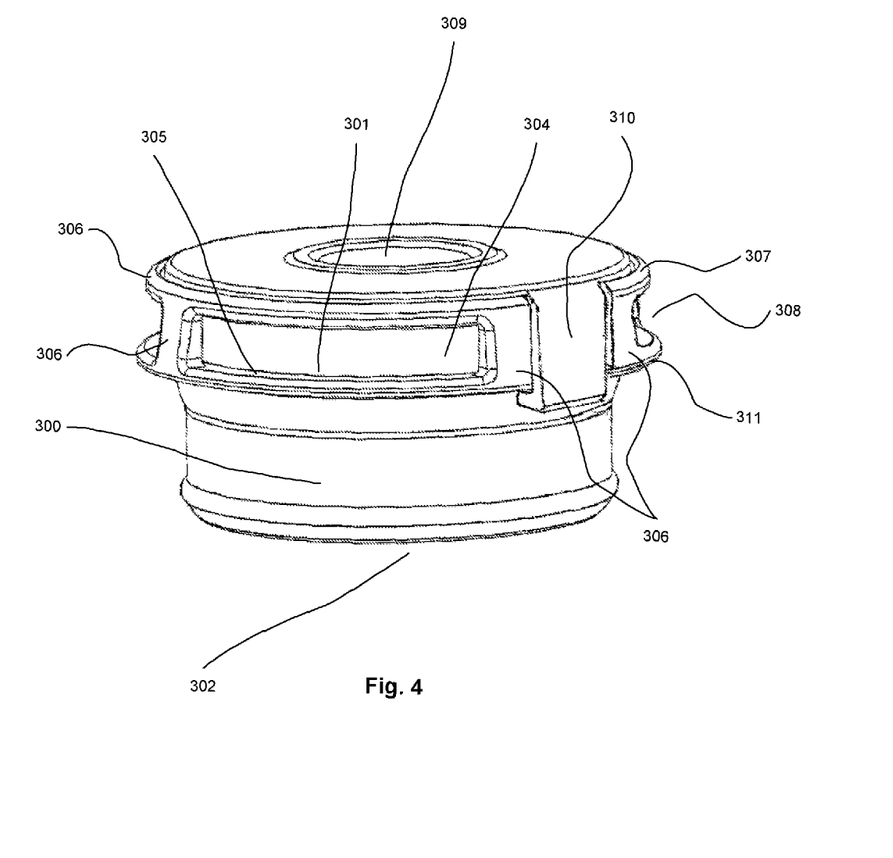
FIG. 4 is an elevated view of the breathing protector according to one embodiment of the present invention.

The device according to another embodiment of the invention is shown in FIG. 4, said device comprising a cylindrical filter housing 300. The device may be a breathing protector for use in a stoma of a laryngectomized or tracheotomised person.

The cylindrical filter housing 300 has a distal and a proximal end, and a central axis from one end to the other. The cylindrical filter housing 300 has a first opening 301 and a second opening 302, such that an air flow during inhalation will pass from the surroundings of a patient through said first opening 301 to said second opening 302, into trachea of said patient, in accordance with the embodiments disclosed in FIGS. 1 to 3. The second opening 302 is located in the proximal end of the device. The second opening 302 may thus be located in a proximal end of said filter housing 300, and said first opening 301 is located distally of said second opening 302, such that said first opening 301 is located upstream said second opening 302 during inhalation. A heat-moisture exchanging filter 303 is received in said cylindrical filter housing 300. The second opening 302 of the filter housing 300 may be provided with radial or diagonal arms, forming a stop element for the heat-moisture exchanging filter 303. The openings between the radial or diagonal arms and the periphery of the second opening 302 constitute outlets of breathing air during inhalation, and consequently inlets of breathing air during exhalation. This is also in line with the embodiments disclosed in FIGS. 1 to 3.

Distally of the second opening 302 of the cylindrical filter housing 300 the first opening 301 is provided. The heat-moisture exchanging filter 303 will then be partly located within said first and second opening when the device is in an open position, and fully located within said first and second opening, when the device is in a closed position. The first opening is encircled by a valve seat 305, corresponding to the valve seat 105, 205 in FIGS. 1 to 3. Thus, the valve seat 305 is arranged around the first opening 301. Radially and/or circumferentially outwards from the valve seat 305, a rail is extending axially and distally from said first opening 301. The rail comprises ribs 306, extending axially and distally from the first opening 301. Bars 307 connects the ribs 306 in the distal end of the device. Between the ribs 306, proximally of the ring 207 apertures 308 are provided. Apertures 308 constitute outlets of breathing air during exhalation, and consequently inlets of breathing air during inhalation. The heat-moisture exchanging filter 303 is located in said housing 300 in between the apertures 308 and the second opening 302, such that the air flow will pass through said heat-moisture exchanger 303, when said air flow during inhalation passes through said apertures 308 to said second opening 302.

Substantially in the same transversal plane as the bars 307 and distally of the valve seat 305 a valve member, such as circular lid 309, is provided. The circular lid 309 has a surface area covering the first opening 301, such that the circular lid 309 peripherally will sit or rest on valve seat 305 to close the first opening 301. The circular lid 309 has a diameter allowing for axial displacement, while said circular lid 309 being arranged in a transversal plane in respect of the cylindrical filter housing 300, within the ribs 306.

The circular lid 309 is provided with at least two peripheral hook elements 310, extending proximally at the edge of the lid 309. The hook elements 310 are configured to grip around the lip 311, to hold the lid in place, whereby axial movement in the distal direction of the lid 309 is hindered when the hook elements 310 engage the lip 311. The lid/valve member 309 is thus hindered from distal movement by the hook elements 310 in the open position. The hook elements 310 runs in through slots in the rail, said through slots having an open end in the distal end of the rail.

It is however also possible for the hook elements 310 to extend through apertures 108, proximally of the ring 107, to thereafter grip around the lip 311, in an embodiment being a combination of the embodiments disclosed in FIG. 1 and FIG. 4.

The heat-moisture exchanging filter 303 is of a flexible/resilient material, such as a resilient foam. Furthermore, the size of heat-moisture exchanging filter 303 is adapted to press the lid 309 distally until the hook elements 310 engage with the lip 311 stopping axial and distal movement of the lid 309. Thus, the heat-moisture exchanging filter 303 acts both as heat-moisture exchanger and return spring, pressing the lid 309 axially and distally into the open position, in accordance with the heat-moisture exchanging filter 103, 203 in FIGS. 1 to 3. The hook elements 310 and the lid 309, due to the shape thereof, holds heat-moisture exchanging filter 303 in position, while the heat-moisture exchanging filter 303 simultaneously acts as a return spring so that the lid 309 after the pressure having been relieved will resiliently return to an open position thereof.

In accordance with the previous embodiments, the ribs 306 of the rail according to the embodiment in FIG. 4 reduces the risk of the valve member being inadvertently closed, since a force in an axial and proximal direction within the ribs 306 has to be applied to close the valve member. Since the lid 309, in the starting position thereof, is in close contact with the heat-moisture exchanging filter 303, the volume of the heat-moisture exchanging filter 303 may be maximized in the device, and breathing air can pass through the apertures 308 directly into contact with the heat-moisture exchanging filter 303 when the device is open, i.e. when the lid 309 is in the outer non-actuated position thereof.

Preferably, the hook elements 310 are provided at opposite positions around the lid 309, whereby the function of maintaining the lid within a centralized position, and also in level with and proximal of the distal ends of the ribs 306 may be improved.

In another embodiment the lid 309 comprises a single hook element 310, whereby the action of maintaining the lid 309 in place is obtained by the combination of the hook element 310 according to FIG. 4 and at least one protrusion 110, according to FIGS. 1 and 2, said protrusion cooperating with the apertures 308.

The heat-moisture exchanging filter 303 is a heat-moisture exchanger filter in accordance with the heat-moisture changing filter 103, 203 according to the embodiments in FIGS. 1 to 3. The material of the heat-moisture exchanger should include flow passages therein, and should have an open structure in which the flow passages are randomly oriented. The material may comprise paper, foamed plastics, wadding made of different fibres, or combinations thereof, having adequate resiliency to push the lid 109, 209, 309 towards the ring 107, flexible cover 210, or bars 307, respectively. It may also be impregnated with a moisture absorbing substance. Furthermore, it is advantageous if the pores or interstices in the material do not have any special direction, such that the breathing air easily may pass through the material in a number of directions in order to achieve the intended deflection.

According to one embodiment the ribs 106, 206, 306 are not connected by a ring, such as ring 107, 207, or bars 307. Instead, the ribs 106, 206, 306 may be angled inwards in the distal end thereof, to enclose the lid 109, 209, 309 within the ribs 106, 206, 306. When the ribs 206 not are connected by ring 207, the flexible cover 210 may be attached directly to the ribs 206.

In one embodiment the valve member 109, 309 or the flexible material 210 of the device is provided with a central boss 111, 211 at the outer pushing surface of the breathing protector, said pushing surface facing the surroundings during use. The central boss 111, 211 provides guidance for the user where to push to obtain the best closing effect of the device.

The device according to the embodiments of the invention may then inserted into a holder of known configuration for application to a tracheostoma.

In the embodiments described above, a breathing protector for use in a stoma of a laryngectomized or tracheotomised person has been described. This breathing protector is configured with at least one inlet and at least one outlet, such that an air flow in use will pass from the surroundings of said person through said inlet to said outlet, into trachea of said person. It is obvious to the skilled artisan, even if it has not been specifically disclosed, that the inlets and outlets may be divided into an increased amount by merely dividing the specific inlets and outlets already disclosed.

The elements and components of the embodiments of the invention may be physically, functionally and logically implemented in any suitable way. Indeed, the functionality may be implemented in a single unit, in a plurality of units or as part of other functional units. As such, the invention may be implemented in a single unit, or may be physically and functionally distributed between different units.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A breathing protector to be fitted in a tracheostoma, comprising:
   a filter housing having a central axis, a distal end, a proximal end, a first opening, and a second opening, wherein the second opening is located in a proximal end of the filter housing, and the first opening is located distally of the second opening, such that the first opening is located upstream of the second opening during inhalation;
   a heat-moisture exchanging filter received in said filter housing wherein said heat-moisture exchanging filter is resilient;
   a valve seat extending around the first opening;
   a rail, located circumferentially of said valve seat, extending axially and distally away from said first opening, the rail including a distal end and at least one rib extending axially and distally away from the first opening and at least one aperture perpendicular to the central axis;
   a valve member, arranged in a transversal plane to the central axis, adapted to engage the valve seat in a closed position, the valve member being reciprocatingly arranged within the rail between the closed position and an open position; and
   wherein the heat-moisture exchanging filter presses the valve member axially and distally into the open position.

2. The breathing protector according to claim 1 further comprising at least one hook element peripherally arranged at the edge of the valve member, the hook element gripping around a lip on the housing and configured to prevent distal movement of the valve member.

3. The breathing protector according to claim 2, wherein the at least one hook elements extends into through slots defined by the rail, the through slots having an open end in the distal end of the rail.

4. The breathing protector according to claim 1, wherein a side wall of the rail includes a plurality of ribs and apertures defined there between.

5. The breathing protector according to claim 4, further comprising a ring connecting the ribs, and wherein the valve member includes protrusions, protrusions engaging with the apertures to stop the axial movement in a distal direction of the valve member.

6. The breathing protector according to claim 1, wherein the rail includes a ring configured to connect a plurality of ribs and an opening of the ring is configured to prevent the valve member to pass there through.

7. The breathing protector according to claim 1, wherein the valve member is attached to the distal end of the rail by a flexible material.

8. The breathing protector according to claim 7, wherein a side wall of the rail includes a plurality of ribs, apertures defined there between, and a ring connecting the ribs, wherein the flexible material is attached to the ring.

9. The breathing protector according to claim 7, wherein the valve member includes protrusions, protrusions engaging the apertures to stop the axial movement in a distal direction of the valve member.

10. The breathing protector according to claim 1, wherein the rail includes a ring having an opening that prevents the valve member to pass there through, and the at least one rib includes a plurality of ribs that are connected to one another by the ring.

11. The breathing protector according to claim 1, wherein the second opening of the filter housing is provided with a plurality of arms disposed parallel to one another and forming a stop element for the heat-moisture exchanging filter.

12. The breathing protector according to claim 1, wherein the valve member includes a central boss at an outer pushing surface of the breathing protector, pushing surface facing radially outwardly of the valve member during use.

13. The breathing protector according to claim 12, wherein a side wall of the rail includes a plurality of ribs and apertures defined there between.

14. The breathing protector according to claim 13, further comprising a ring connecting the ribs, and wherein the valve member includes protrusions, the protrusions engaging with the apertures to stop the axial movement in a distal direction of the valve member.

15. The breathing protector according to claim 12, wherein the second opening of the filter housing is provided with a plurality of arms disposed parallel to one another and forming a stop element for the heat-moisture exchanging filter.

16. The breathing protector according to claim 12, wherein the heat-moisture exchanging filter uninterruptedly contacts the valve member when the valve member is disposed in the open position and when the valve member is disposed in the closed position.

17. The breathing protector according to claim 16, wherein the heat-moisture exchanging filter fills a volume defined between the valve member and the proximal end of the filter housing when the valve member moves between the open and closed positions.

18. The breathing protector according to claim 1, wherein the heat-moisture exchanging filter uninterruptedly contacts the valve member when the valve member is disposed in the open position and when the valve member is disposed in the closed position.

19. The breathing protector according to claim 18, wherein the heat-moisture exchanging filter fills a volume defined between the valve member and the proximal end of the filter housing when the valve member moves between the open and closed positions.

\* \* \* \* \*